United States Patent
Nakauchi et al.

(10) Patent No.: US 11,759,182 B2
(45) Date of Patent: Sep. 19, 2023

(54) ULTRASOUND DIAGNOSTIC APPARATUS AND METHOD OF REDUCING POWER CONSUMPTION

(71) Applicant: Canon Medical Systems Corporation, Otawara (JP)

(72) Inventors: Nobuyuki Nakauchi, Otawara (JP); Yoshitaka Watanabe, Utsunomiya (JP); Shigeru Akiyama, Nasushiobara (JP); Taketoshi Nagai, Nasushiobara (JP); Jaeho Choi, Utsunomiya (JP); Yasuhiro Takahashi, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 497 days.

(21) Appl. No.: 16/009,789

(22) Filed: Jun. 15, 2018

(65) Prior Publication Data
US 2018/0368811 A1    Dec. 27, 2018

(30) Foreign Application Priority Data
Jun. 23, 2017 (JP) ................. 2017-122908

(51) Int. Cl.
  *A61B 8/00* (2006.01)
  *A61B 8/08* (2006.01)
(52) U.S. Cl.
  CPC .............. *A61B 8/54* (2013.01); *A61B 8/5207* (2013.01); *A61B 8/56* (2013.01)
(58) Field of Classification Search
  CPC ........... A61B 8/54; A61B 8/5207; A61B 8/56; A61B 8/06; A61B 8/44; A61B 8/4444;
  (Continued)

(56) References Cited

U.S. PATENT DOCUMENTS 6,450,958 B1 *  9/2002  Linkhart ............... A61B 8/00
                                              600/437
2016/0306032 A1 * 10/2016  Schwarz ............... G01S 7/4812
(Continued)

FOREIGN PATENT DOCUMENTS

CN    1281294 A      1/2001
CN    1395368 A   *  2/2003  ............... G06F 1/04
(Continued)

OTHER PUBLICATIONS

Combined Chinese Office Action and Search Report dated Jun. 24, 2020 in corresponding Chinese Patent Application No. 201810650810.X (with English Translation of Category of Cited Documents), 12 pages.
(Continued)

*Primary Examiner* — Christopher Koharski
*Assistant Examiner* — Marjan Saboktakin
(74) *Attorney, Agent, or Firm* — Oblon, McClelland, Maier & Neustadt, L.L.P.

(57) ABSTRACT

According to one embodiment, an ultrasound diagnostic apparatus includes at least one circuitry, and control circuitry. The at least one circuitry is used for an ultrasound scan. The control circuitry is configured to reset the at least one circuitry upon receipt of a stop instruction to stop the ultrasound scan and to stop supply of a clock to the at least one circuitry.

4 Claims, 9 Drawing Sheets (58) Field of Classification Search
CPC ......... A61B 8/465; A61B 8/488; A61B 8/565; A61B 8/543; A61B 8/554; G16H 40/60; G01S 7/4861
See application file for complete search history.

(56) References Cited

U.S. PATENT DOCUMENTS

2017/0252013 A1* 9/2017 Choi ................. A61B 8/54
2018/0338746 A1* 11/2018 Wu .................... A61B 8/54

FOREIGN PATENT DOCUMENTS

| CN | 1395368 A | 2/2003 | | |
| CN | 202363365 U | 8/2012 | | |
| CN | 104757998 A | 7/2015 | | |
| JP | 5-253225 | 10/1993 | | |
| JP | 2000-70262 | 3/2000 | | |
| JP | 2000070262 A | * 3/2000 | ......... | G01S 7/52096 |
| JP | 2003-175035 | 6/2003 | | |
| JP | 2006-174854 | 7/2006 | | |
| JP | 2007-195683 | 8/2007 | | |
| JP | 2013-90839 | 5/2013 | | |
| JP | 2014-97249 | 5/2014 | | |
| JP | 2015-6249 | 1/2015 | | |

OTHER PUBLICATIONS

Wang Zhongming et al., "Remote Control System Analysis and FC Bus System Maintenance (First)", Changhong T2982 Color TV, Jul. 2001, 3 pages (with English Translation).
Combined Chinese Office Action and Search Report dated Feb. 22, 2021 in Patent Application No. 201810650810.X (with English translation of Category of Cited Documents), 12 pages.

* cited by examiner

ULTRASOUND DIAGNOSTIC APPARATUS AND METHOD OF REDUCING POWER CONSUMPTION

CROSS-REFERENCE TO RELATED APPLICATIONS

This application is based upon and claims the benefit of priority from the prior Japanese Patent Application No. 2017-122908, filed Jun. 23, 2017, the entire contents of which are incorporated herein by reference.

FIELD

Embodiments described herein relate generally to an ultrasound diagnostic apparatus, and a method of reducing power consumption.

BACKGROUND

Ultrasound diagnostic apparatuses have a freeze function for pausing a displayed ultrasound image. Usually, when the freeze function is turned on, an ultrasound scan is stopped; however, a system clock is continued to be supplied to the circuitry included in the ultrasound diagnostic apparatus and used for the ultrasound scan, and at least power for the clock supply is continued to be consumed. It is therefore conceivable to stop supply of the clock to the circuitry used for the ultrasound scan while the freeze function is ON.

If a mere stop/restart of supply of a clock is performed in accordance with ON/OFF of the freeze function, circuitry including a phase-locked loop (PLL) is not supplied with a stable clock for a while after restart. Therefore, circuitry including a phase-locked loop is likely to malfunction when the freeze function is switched from ON to OFF, i.e., when the ultrasound scan is restarted.

DETAILED DESCRIPTION

According to one embodiment, an ultrasound diagnostic apparatus includes at least one circuitry, and control circuitry. The at least one circuitry is used for an ultrasound scan. The control circuitry is configured to reset the at least one circuitry upon receipt of a stop instruction to stop the ultrasound scan and to stop supply of a clock to the at least one circuitry.

Hereinafter, embodiments will be described with reference to drawings.

First Embodiment

Figure 1:
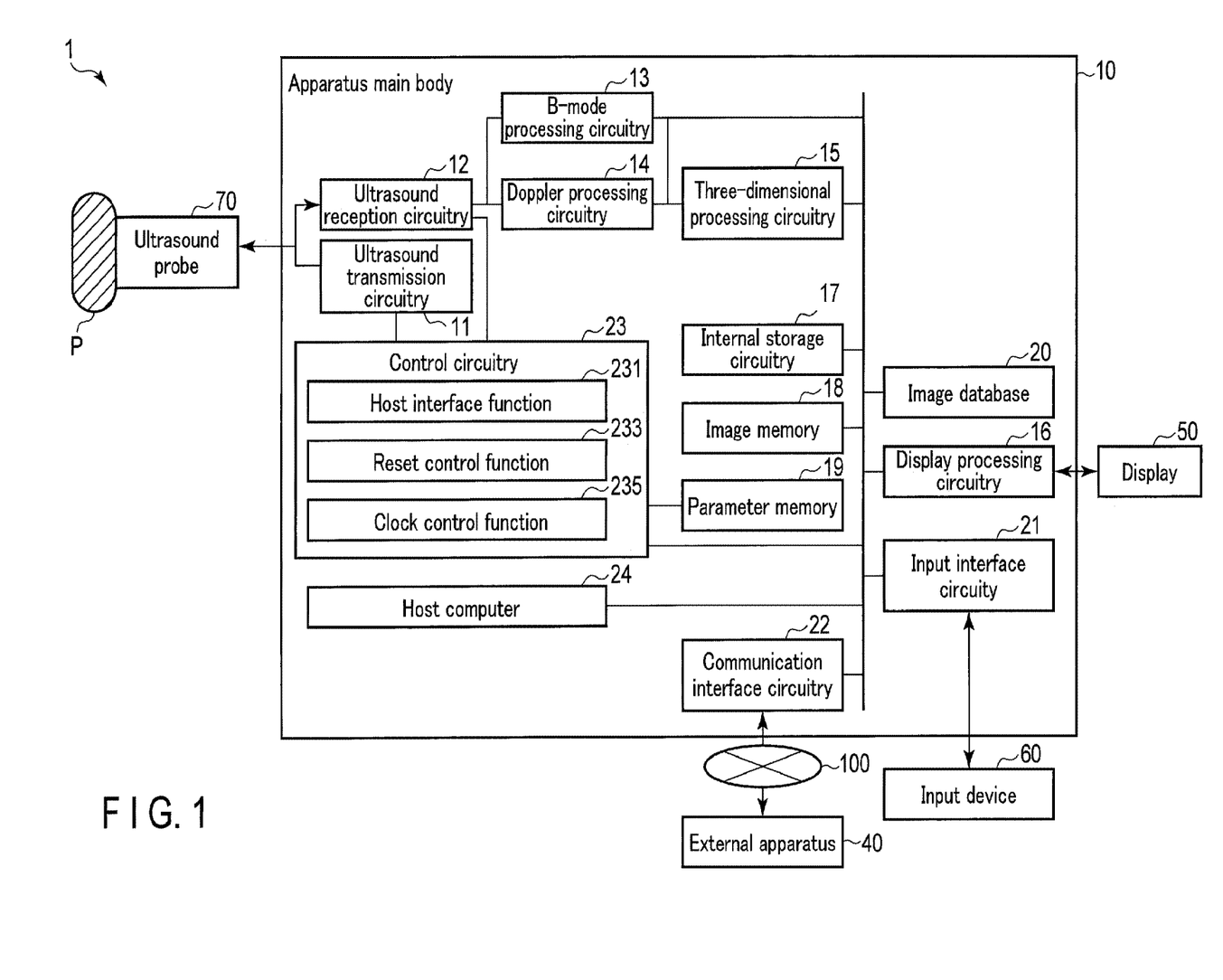
FIG. 1 is a diagram showing a configuration of an ultrasound diagnostic apparatus according to a first embodiment.

An ultrasound diagnostic apparatus 1 according to a first embodiment will be described with reference to the block diagram of FIG. 1. As shown in FIG. 1, the ultrasound diagnostic apparatus 1 comprises an apparatus main body 10, an ultrasound probe 70, a display 50, and an input device 60. The apparatus main body 10 is connected to an external apparatus 40 via a network 100. The apparatus main body 10 is connected to the display 50 and the input device 60.

The ultrasound probe 70 includes, for example, a plurality of piezoelectric vibrators, a matching layer provided in each piezoelectric vibrator, and a backing member for preventing backward propagation of ultrasound from the piezoelectric vibrators. The ultrasound probe 70 is detachably attached to the apparatus main body 10. The piezoelectric vibrators generate ultrasound based on a drive signal supplied from ultrasound transmission circuitry 11 included in the apparatus main body 10. The ultrasound probe 70 is provided with a freeze button pressed when switching ON/OFF the freeze function for stopping an ultrasound scan and displaying an ultrasound image immediately before the stop of the ultrasound scan.

When ultrasound is transmitted from the ultrasound probe 70 to a subject P, the transmitted ultrasound is reflected by one after another discontinuous surfaces having acoustic impedances in body tissue of the subject P, and is received at the piezoelectric vibrators included in the ultrasound probe 70 as a reflected wave signal. The amplitude of the received reflected wave signal depends on the difference in acoustic impedances of the discontinuous surfaces by which ultrasound is reflected. The reflected wave signal of the case where the transmitted ultrasound pulse is reflected by flowing blood or by a surface like a cardiac wall, is subjected to a frequency shift by the Doppler effect while depending on the velocity component in the ultrasound transmission direction of a moving object. The ultrasound probe 70 receives the reflected wave signal from the subject P, and converts it into an electrical signal. The ultrasound probe 70 is, for example, a one-dimensional array probe in which a plurality of ultrasound vibrators are arranged in a predetermined direction. The ultrasound probe 70 is not limited to the one-dimensional array probe, and may be a two-dimensional array probe (probe in which a plurality of ultrasound vibrators are arranged in a two-dimensional matrix), a mechanical four-dimensional probe (probe capable of performing an ultrasound scan while mechanically flapping the ultrasound vibrator line in directions orthogonal to the alignment direction), or the like.

The apparatus main body 10 shown in FIG. 1 is an apparatus that generates an ultrasound image based on the reflected wave signal received by the ultrasound probe 70. The apparatus main body 10 includes ultrasound transmission circuitry 11, ultrasound reception circuitry 12, B-mode processing circuitry 13, Doppler processing circuitry 14, three-dimensional processing circuitry 15, display processing circuitry 16, internal storage circuitry 17, an image memory 18 (cine-memory), a parameter memory 19, an image database 20, input interface circuitry 21, communication interface circuitry 22, control circuitry 23, and a host computer 24, as shown in FIG. 1.

The ultrasound transmission circuitry 11 is a processor that supplies the ultrasound probe 70 with a drive signal. The ultrasound transmission circuitry 11 is realized by, for example, a trigger generation circuit, a delay circuit, a pulser circuit, and a PLL. The trigger generation circuitry repeatedly generates a rate pulse for forming transmitted ultrasound at a predetermined rate frequency under control of the control circuitry 23. The delay circuitry provides each rate pulse generated by the trigger generation circuitry with a delay time for each piezoelectric vibrator necessary for converging ultrasound generated by the ultrasound probe 70 in a beam form, and for determining transmission directivity. The pulser circuitry applies a drive signal (drive pulse) to the ultrasound probe 70 with a timing based on the rate pulse under control of the control circuitry 23. The delay circuit varies the delay time to be provided to each rate pulse, whereby the transmission direction from the piezoelectric vibrator surface can be freely adjusted.

The ultrasound reception circuitry 12 is a processor that performs various processes on the reflected wave signal received by the ultrasound probe 70 to generate a received signal. The ultrasound reception circuitry 12 is realized by, for example, amplifier circuitry, an A/D converter, reception delay circuitry, an adder, and a PLL. The amplifier circuitry performs a gain correction process by amplifying the reflected wave signal received by the ultrasound probe 70 for each channel. The A/D converter converts the gain-corrected reflected wave signal into a digital signal. The reception delay circuitry provides the digital signal with a delay time necessary for determining reception directivity. The adder adds up a plurality of digital signals provided with delay times. By the adding process of the adder, a received signal with an enhanced reflected component in a direction corresponding to the reception directivity is generated.

The B-mode processing circuitry 13 is a processor that generates B-mode data based on the received signal received from the ultrasound reception circuitry 12. The B-mode processing circuitry 13 performs an envelope wave detecting process, and a logarithmic amplifying process, etc. on the received signal received from the ultrasound reception circuitry 12 to generate data (B-mode data) that expresses signal intensity by brightness. The generated B-mode data is stored in a raw data memory (not shown) as B-mode raw data on a two-dimensional ultrasound scan line.

The Doppler processing circuitry 14 is a processor that generates a Doppler wave and Doppler data based on the received signal received from the ultrasound reception circuitry 12. The Doppler processing circuitry 14 extracts a blood-flow signal from the received signal, and generates a Doppler wave from the extracted blood-flow signal, as well as generating data (Doppler data) obtained by extracting from the blood-flow signal information on, for example, average velocity, distribution, and power at multiple points. The generated Doppler data is stored in a raw data memory (not shown) as Doppler raw data on a two-dimensional ultrasound scan line.

The three-dimensional processing circuitry 15 is a processor capable of generating various volume data based on the data generated by the B-mode processing circuitry 13 and the Doppler processing circuitry 14.

For example, the three-dimensional processing circuitry 15 performs a raw-voxel conversion, including an interpolating process into which spatial positional information is factored on the B-mode data stored in the raw data memory, to generate B-mode volume data representing form information. The three-dimensional processing circuitry 15 also performs a raw-voxel conversion, including an interpolating process into which spatial positional information is factored on the Doppler data stored in the raw data memory, to generate blood flow (color Doppler) volume data representing blood flow information. B-mode volume data and blood flow volume data are constituted by voxels in a desired range.

The three-dimensional processing circuitry 15 also performs a rendering process on the generated various volume data to generate rendering image data.

The display processing circuitry 16 is a processor that causes the display 50 to display various images. The display processing circuitry 16 generates ultrasound image data as a display image by, for example, a coordinate conversion process. The coordinate conversion process is a process for converting, for example, a signal sequence of a scanning line of an ultrasound scan which is constituted by B-mode data and Doppler data into a video signal which is a scanning line signal sequence in a common video format representatively used by television. The generated ultrasound image data is converted into data in, for example, a digital imaging and communication in medicine (DICOM)-compliant format, and is stored in, for example, the image database 20.

The display processing circuitry 16 generates B-mode image data based on the B-mode raw data stored in the raw data memory. The B-mode image data has a pixel value (brightness value) reflecting, for example, characteristics of the ultrasound probe, such as sound convergence, and sound-field characteristics of an ultrasound beam (e.g., a transmitted/received beam). For example, B-mode image data has a relatively higher brightness in the vicinity of the focus of ultrasound than in the unfocused part in the scanned area. The display processing circuitry 16 causes the display 50 to display the generated B-mode image data as an ultrasound image.

The display processing circuitry 16 also generates Doppler image data relating to an average speed image, a distribution image, and a power image, etc. based on the Doppler raw data stored in the raw data memory. The display processing circuitry 16 causes the display 50 to display the generated Doppler image data as an ultrasound image.

The display processing circuitry 16 also converts image data into a video signal by performing various processes, such as dynamic range, brightness, contrast, γ curve corrections, and an RGB conversion, on various image data generated at the three-dimensional processing circuitry 15. The display processing circuitry 16 causes the display 50 to display the video signal as an ultrasound image.

The display processing circuitry 16 may generate a user interface (graphical user interface: GUI) for the operator (such as a person performing surgery), or the like to input various instructions by the input interface circuitry 21, and cause the display 50 to display the GUI. As the display 50, for example, a CRT display, a liquid crystal display, an organic EL display, an LED display, a plasma display, or any other display known in the relevant technical field may be used as appropriate.

The internal storage circuitry 17 includes, for example, a magnetic or optical storage medium, or a storage medium readable by a processor such as a semiconductor memory. The internal storage circuitry 17 stores, for example, a control program for realizing ultrasound transmission and reception, a control program for performing image processing, and a control program for performing display processing. The internal storage circuitry 17 also stores a control program for realizing various functions according to the present embodiment. The internal storage circuitry 17 also stores diagnostic information (such as a patient's ID, and a doctor's observation), a diagnostic protocol, a body mark generation program, and a data group such as a conversion table in which the range of color data used for imaging is preset for each diagnostic site. The internal storage circuitry 17 may also store an anatomical picture, such as an atlas, concerning the structure of an organ in a living body.

The internal storage circuitry 17 also stores volume data and rendering image data generated at the three-dimensional processing circuitry 15, in accordance with a storing operation input through the input interface circuitry 21. The internal storage circuitry 17 may store the volume data and rendering image data generated at the three-dimensional processing circuitry 15 together with the operation order and operation time, in accordance with a storage operation input through the input interface circuitry 21. The internal storage circuitry 17 may transfer the stored data to an external apparatus via the communication interface circuitry 22.

The image memory 18 includes, for example, a magnetic or optical storage medium, or a storage medium readable by a processor such as a semiconductor memory. The image memory 18 stores image data corresponding to a plurality of frames immediately before the freeze function is turned on by an input via the input interface circuitry 21. The image data stored in the image memory 18 is, for example, continuously displayed (cine-displayed).

The parameter memory 19 includes, for example, a storage medium readable at high speed by a processor, such as a semiconductor memory. The parameter memory 19 is, for example, a main memory. The parameter memory 19 stores a parameter (hereinafter referred to as a control parameter) necessary for starting an ultrasound scan. The control parameter includes, for example, probe selection data, gain data, and a decimation (thinning-out) filter coefficient. The probe selection data is, for example, data representing a probe selected before the ultrasound scan is stopped. The gain data is, for example, data representing a gain value before the ultrasound scan is stopped. The decimation filter coefficient is, for example, a decimation filter coefficient that was set before the ultrasound scan is stopped.

The image database 20 stores image data transferred from the external apparatus 40. For example, the image database 20 obtains from the external apparatus 40 and stores historical image data concerning the same patient obtained from the past medical examination. The historic image data includes ultrasound image data, computed tomography (CT) image data, MR image data, position emission tomography (PET)-CT image data, PET-MR image data, and X-ray image data. The historic image data is stored as, for example, three-dimensional volume data and rendering data.

The image database 20 may store desired image data by reading image data stored in a storage medium such as an MO, a CD-R, or a DVD.

The input interface circuitry 21 receives various instructions from the operator via the input device 60. The input device 60 includes, for example, a mouse, a keyboard, a panel switch, a slider switch, a dial switch, a track ball, a rotary encoder, an operation panel, and a touch command screen (TCS). The input interface circuitry 21 receives various instructions from the operator via a freeze button provided in the ultrasound probe 70.

The input interface circuitry 21 is connected to the host computer 24 via, for example, a bus, converts an operation instruction input by the operator into an electrical signal, and outputs the electrical signal to the host computer 24. In the present specification, the input interface circuitry 21 is not limited to circuitry connected to a physical operational component, such as a mouse or a keyboard. For example, processing circuitry that receives, as a wireless signal, an electrical signal corresponding to an operation instruction input from an external input device provided separately from the ultrasound diagnostic apparatus 1, and outputs the electrical signal to the host computer 24, is also an example of the input interface circuitry 21.

The communication interface circuitry 22 is connected to the external apparatus 40 via, for example, the network 100, and performs data communication with the external apparatus 40. The external apparatus 40 is, for example, a database of a picture archiving and communication system (PACS), which is a system that manages data of various medical images, and a database of an electronic health record system, which manages electronic health records accompanied with medical images. The external apparatus 40 is also, for example, various medical image diagnostic apparatuses other than the ultrasound diagnostic apparatus 1 according to the present embodiment, such as an X-ray CT apparatus, a magnetic resonance imaging (MRI) apparatus, a nuclear medicine diagnostic apparatus, and an X-ray diagnostic apparatus. The standard of the communication with the external apparatus 40 may be any standard, but is, for example, DICOM.

The control circuitry 23 is, for example, a processor that controls operations relating to an ultrasound scan. The control circuitry 23 performs an operation program stored in the internal storage circuitry 17, thereby realizing a function corresponding to the operation program. Specifically, the control circuitry 23 has a host interface function 231, a reset control function 233, and a clock control function 235.

The host interface function 231 is a function of performing various operations based on various instructions from the host computer 24. When the host interface function 231 is performed, the control circuitry 23 receives, for example, a setting instruction to set a control parameter from the host computer 24. Based on the received setting instruction, the control circuitry 23 performs setting of a control parameter for the ultrasound transmission circuitry 11 and for the ultrasound reception circuitry 12.

The reset control function 233 is a function of resetting each circuitry included in the ultrasound diagnostic apparatus 1 or canceling the reset of each circuitry. When the reset control function 233 is performed, the control circuitry 23 resets, for example, the ultrasound transmission circuitry 11 and the ultrasound reception circuitry 12. The control circuitry 23 also cancels the reset of the ultrasound transmission circuitry 11 and the reset of the ultrasound reception circuitry 12, for example.

Resetting circuitry in the present embodiment means, for example, fixing a switching element included in each circuitry included in the ultrasound diagnostic apparatus 1 in a predetermined initial state preset for each circuitry of the high state (such as a state in which a predetermined electric potential is maintained) and the low state (such as a state in which the electric potential is zero). Data stated in the register included in each circuitry is thereby deleted.

Canceling the reset of circuitry in the present embodiment means, for example, the state in which the state of a switching element included in each circuitry included in the ultrasound diagnostic apparatus 1 can be changed.

The clock control function 235 is a function of starting or stopping the supply of a clock to each circuitry included in the ultrasound diagnostic apparatus 1. When the clock control function 235 is performed, the control circuitry 23 stops the supply of a clock, for example, to the ultrasound transmission circuitry 11 and to the ultrasound reception circuitry 12 based on an instruction to stop an ultrasound scan from, for example, the host computer 24. The control circuitry 23 also starts the supply of a clock, for example, to the ultrasound transmission circuitry 11 and to the ultrasound reception circuitry 12 based on an instruction to start an ultrasound scan from, for example, the host computer 24.

The host interface function 231, the reset control function 233, and the clock control function 235 may be incorporated as control programs; otherwise, dedicated hardware circuits capable of performing respective functions may be incorporated in the control circuitry 23 itself or the apparatus main body 10 as circuits that can be referred to by the control circuitry 23.

The host computer 24 includes a processor, and functions as the nerve center of the ultrasound diagnostic apparatus 1. Based on a reception signal generated by the ultrasound reception circuitry 12, the host computer 24 controls, for example, the B-mode processing circuitry 13, the Doppler processing circuitry 14, the three-dimensional processing circuitry 15, and the display processing circuitry 16, generates predetermined ultrasound image data, and causes the display 50 to display the generated ultrasound image data. The host computer 24 receives various instructions from the operator or the like via the input interface circuitry 21. The host computer 24 inputs the received various instructions to the control circuitry 23.

Next, operations of the ultrasound diagnostic apparatus 1 according to the first embodiment will be described with reference to the drawings.

Figure 2:
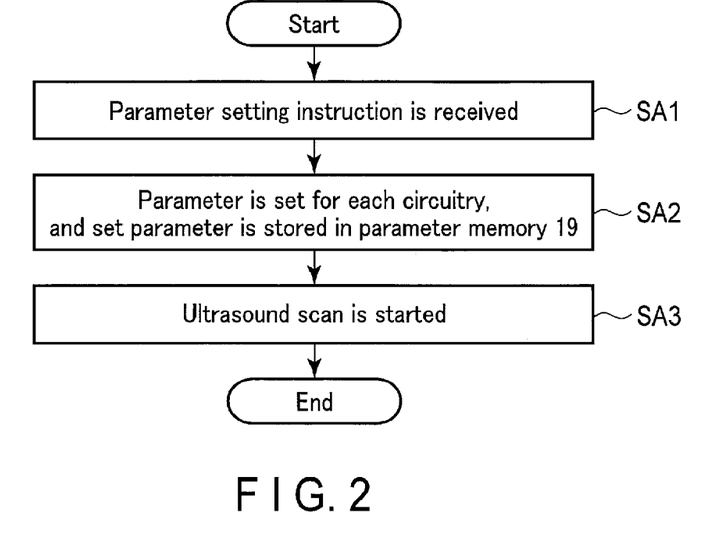
FIG. 2 is a flowchart showing an operation of control circuitry performed when the ultrasound diagnostic apparatus according to the first embodiment sets a parameter for each circuitry.

First, an operation of the ultrasound diagnostic apparatus 1 performed when a parameter setting instruction is received will be described. FIG. 2 is a flowchart showing an operation of the control circuitry performed when the ultrasound diagnostic apparatus 1 according to the first embodiment sets a parameter for each circuitry. In the following description, let us assume that a control parameter for each of the ultrasound transmission circuitry 11 and the ultrasound reception circuitry 12 are input to the host computer 24 by the operator or the like via the input interface circuitry 21, and assume that the host computer 24 notifies the control circuitry 23 of a setting instruction to set the input control parameter. Setting of a control parameter is performed, for example, at the time of an initial setting and the time of a setting change.

The control circuitry 23 performs the host interface function 231, and receives from the host computer 24 a setting instruction to set a control parameter (step SA1).

Figure 3:
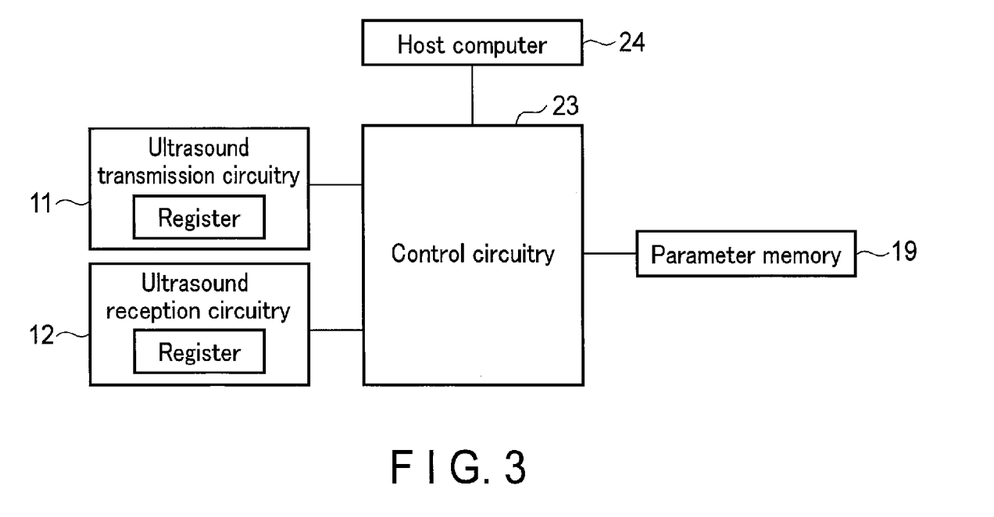
FIG. 3 is a diagram for explaining an operation of the control circuitry performed when the ultrasound diagnostic apparatus according to the first embodiment sets a parameter for each circuitry.

The control circuitry 23 sets a control parameter for each circuitry based on the received setting instruction (step SA2). FIG. 3 is a diagram for explaining an operation of the control circuitry 23 performed when the ultrasound diagnostic apparatus 1 according to the first embodiment sets a parameter for each circuitry. As shown in FIG. 3, the control circuitry 23 writes, via a local bus to the ultrasound transmission circuitry 11, a control parameter in the register included in the ultrasound transmission circuitry 11, based on the setting instruction transmitted from the host computer 24, for example. A control parameter is thereby set for the ultrasound transmission circuitry 11. At this time, the control circuitry 23 stores, via a local bus to the parameter memory 19, a control parameter of the same content as the control parameter set for the ultrasound transmission circuitry 11 in the parameter memory 19. The control circuitry 23 also writes a control parameter in the register included in the ultrasound reception circuitry 12 via a local bus to the ultrasound reception circuitry 12 based on the setting instruction transmitted from the host computer 24, for example. A control parameter is thereby set for the ultrasound reception circuitry 12. At this time, the control circuitry 23 stores a control parameter of the same content as the control parameter set for the ultrasound reception circuitry 12 in the parameter memory 19 via the local bus to the parameter memory 19.

Then, the control circuitry 23 stores, in a predetermined internal memory included in the control circuitry 23, address association information associating a physical address of the control parameter on the register included in each circuitry with a physical address of a parameter of the same content on the parameter memory 19. The stored address association information is required when performing a DMA transfer using the control parameter for each circuitry stored in the parameter memory 19. The address association information may be preset.

Figure 4:
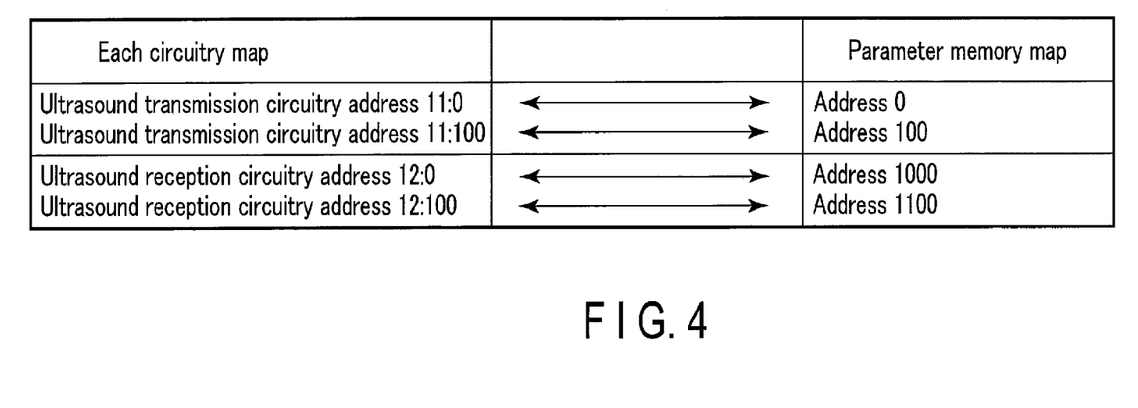
FIG. 4 is a diagram showing the content of address association information according to the first embodiment.

FIG. 4 is a diagram showing an example of the content of the address association information according to the first embodiment. FIG. 4 indicates that parameters having the same content are stored at address 0 of the register included in the ultrasound transmission circuitry 11 and at address 0 of the parameter memory 19, for example. FIG. 4 also indicates that parameters having the same content are stored at address 100 of the register included in the ultrasound transmission circuitry 11, and at address 100 of the parameter memory 19, for example. FIG. 4 also indicates that parameters having the same content are stored at address 0 of the register included in the ultrasound reception circuitry 12, and at address 1000 of the parameter memory 19, for example. FIG. 4 also indicates that parameters having the same content are stored at address 100 of the register included in the ultrasound reception circuitry 12, and at address 1100 of the parameter memory 19, for example.

The control circuitry 23 controls the ultrasound transmission circuitry 11 and the ultrasound reception circuitry 12 to start an ultrasound scan (step SA3).

Figure 5:
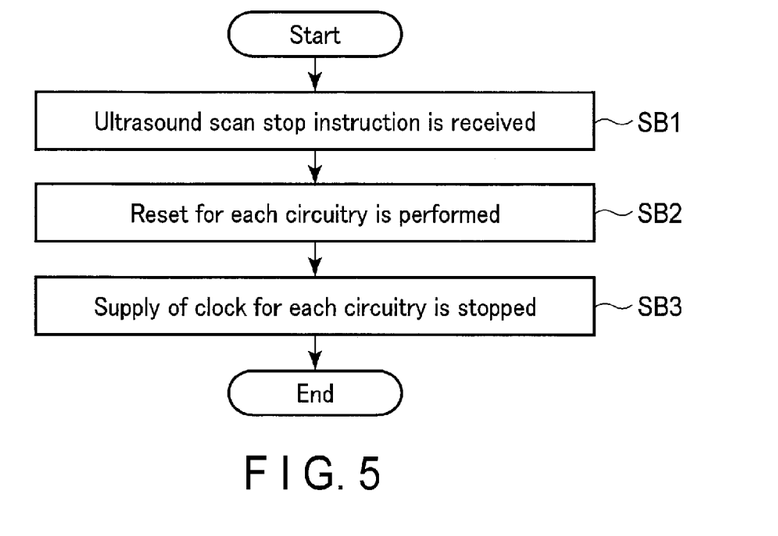
FIG. 5 is a flowchart showing an operation of the control circuitry performed when the ultrasound diagnostic apparatus according to the first embodiment receives a stop instruction to stop an ultrasound scan.
Figure 6:
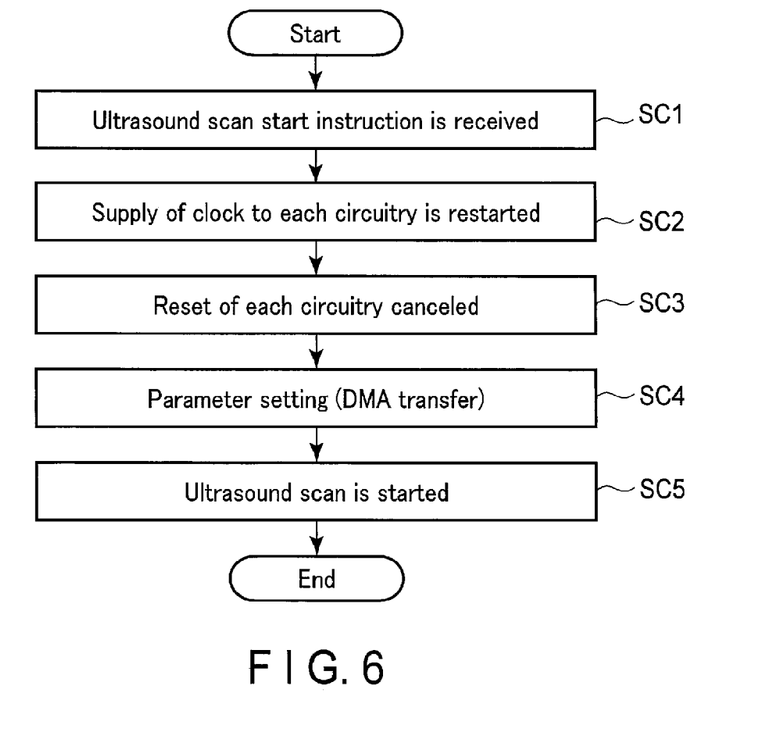
FIG. 6 is a flowchart showing an operation of the control circuitry performed when the ultrasound diagnostic apparatus according to the first embodiment receives a start instruction to start an ultrasound scan.
Figure 7:
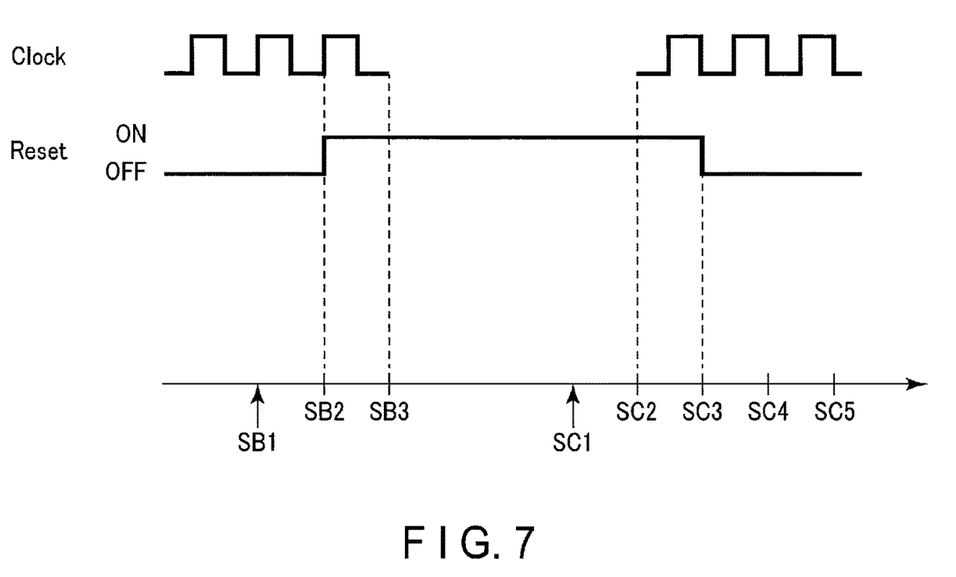
FIG. 7 is a time-sequence diagram for explaining operations of the ultrasound transmission circuitry and the ultrasound reception circuitry corresponding to the operation of the control circuitry in each step of the flowcharts shown in FIGS. 5 and 6.

Next, an operation of the ultrasound diagnostic apparatus 1 performed when an instruction to stop or start an ultrasound scan is received will be described with reference to FIGS. 5, 6, and 7. FIG. 5 is a flowchart showing an operation of the control circuitry 23 performed when the ultrasound diagnostic apparatus 1 according to the first embodiment receives a stop instruction to stop an ultrasound scan. FIG. 6 is a flowchart showing an operation of the control circuitry 23 performed when the ultrasound diagnostic apparatus 1 according to the first embodiment receives a start instruction to start an ultrasound scan. FIG. 7 is a time-sequence diagram for explaining operations of the ultrasound transmission circuitry 11 and the ultrasound reception circuitry 12 corresponding to the operation of the control circuitry 23 in each step of the flowcharts shown in FIGS. 5 and 6.

First, an operation of the ultrasound diagnostic apparatus 1 performed when a stop instruction to stop an ultrasound scan is received will be described with reference to FIGS. 5 and 7. In the following description, let us assume that an operation to turn on the freeze function is performed by pressing the freeze button provided in the ultrasound probe 70, for example. At this time, a stop instruction to stop an ultrasound scan is input to the host computer 24. Then, the host computer 24 notifies the control circuitry 23 of the input stop instruction. The operation to turn on the freeze function may be performed by designating a predetermined area of the TCS included in the input device 60.

In FIG. 5, the control circuitry 23 performs the host interface function 231, and receives from the host computer 24 an instruction to stop an ultrasound scan (step SB1). At this time, the ultrasound transmission circuitry 11 and the ultrasound reception circuitry 12 are provided with a clock as shown in FIG. 7. Furthermore, the ultrasound transmission circuitry 11 and the ultrasound reception circuitry 12 are in a non-reset state as shown in FIG. 7.

In FIG. 5, the control circuitry 23 performs the reset control function 233, and resets each circuitry (step SB2). Specifically, the control circuitry 23 brings all the switching elements included in each circuitry realizing the ultrasound transmission circuitry 11 back to their initial states, for example. At this time, the ultrasound transmission circuitry 11 is reset (brought into a reset-ON state) as shown in FIG. 7. As a result, the control parameter stored in the register included in the ultrasound transmission circuitry 11 is deleted. The control circuit 23 also brings all the switching elements included in each circuitry realizing the ultrasound reception circuitry 12 back to their initial states, for example. At this time, the ultrasound reception circuitry 12 is reset (brought into the reset-ON state) as shown in FIG. 7. As a result, the control parameter stored in the register included in the ultrasound reception circuitry 12 is deleted.

In FIG. 5, after resetting each circuitry, the control circuit 23 performs the clock control function 235, and stops the supply of a clock to each circuitry (step SB3). For example, after resetting the ultrasound transmission circuitry 11, the control circuitry 23 stops the supply of a clock to the ultrasound transmission circuitry 11. At this time, the supply of a clock to the ultrasound transmission circuitry 11 is stopped as shown in FIG. 7. For example, after resetting the ultrasound reception circuitry 12, the control circuitry 23 stops the supply of a clock to the ultrasound reception circuitry 12. At this time, the supply of a clock to the ultrasound reception circuitry 12 is stopped as shown in FIG. 7.

Next, an operation of the ultrasound diagnostic apparatus 1, performed when a start instruction to start an ultrasound scan is received again after an ultrasound scan is stopped, will be described with reference to FIGS. 6 and 7. In the following description, let us assume that an operation to turn off the freeze function is performed by pressing the freeze button provided in the ultrasound probe 70, for example. At this time, a start instruction to start an ultrasound scan is input to the host computer 24. Then, the host computer 24 notifies the control circuitry 23 of the input start instruction.

In FIG. 6, the control circuitry 23 performs the host interface function 231, and receives from the host computer 24 an instruction to start an ultrasound scan (step SC1). At this time, the ultrasound transmission circuitry 11 and the ultrasound reception circuitry 12 are not provided with a clock as shown in FIG. 7. Furthermore, the ultrasound transmission circuitry 11 and the ultrasound reception circuitry 12 are in a reset state as shown in FIG. 7.

In FIG. 6, the control circuitry 23 performs the clock control function 235, and restarts the supply of a clock to the ultrasound transmission circuitry 11 and to the ultrasound reception circuitry 12 (step SC2). At this time, the supply of a clock to the ultrasound transmission circuitry 11 and to the ultrasound reception circuitry 12 is started as shown in FIG. 7.

In FIG. 6, after restarting the supply of a clock to the ultrasound transmission circuitry 11 and to the ultrasound reception circuitry 12, the control circuitry 23 performs the reset control function 233, and cancels the reset of the ultrasound transmission circuitry 11 and the reset of the ultrasound reception circuitry 12 (step SC3). At this time, the reset of the ultrasound transmission circuitry 11 and the reset of the ultrasound reception circuitry 12 are canceled (the ultrasound transmission circuitry 11 and the ultrasound reception circuitry 12 are brought into a reset-OFF state) as shown in FIG. 7. Accordingly, the circuitry realized by a PLL or the like, such as the ultrasound transmission circuitry 11 or the ultrasound reception circuitry 12, can be prevented from malfunctioning when an ultrasound scan is restarted.

In FIG. 6, the control circuitry 23 performs the host interface function 231, refers to address association information stored in the predetermined internal memory included in the control circuitry 23, and reads a control parameter from the parameter memory 19. The read control parameter is the control parameter stored in the parameter memory 19 immediately before the ultrasound scan is stopped. The control circuitry 23 direct memory access (DMA)-transfers the read control parameter to each circuitry. Then, the control circuitry 23 sets a control parameter for each of the ultrasound transmission circuitry 11 and the ultrasound reception circuitry 12 (step SC4). At this time, a control parameter is set for each of the ultrasound transmission circuitry 11 and the ultrasound reception circuitry 12 as shown in FIG. 7. Accordingly, parameter setting can be performed without intervention of the host computer 24. Parameters transferred after the ultrasound scan is started, such as delay data provided to each channel, and aperture-related data, etc., are not DMA-transferred.

In FIG. 6, the control circuitry 23 controls the ultrasound transmission circuitry 11 and the ultrasound reception circuitry 12 to start an ultrasound scan (step SC5). At this time, the ultrasound transmission circuitry 11 and the ultrasound reception circuitry 12 start an ultrasound scan as shown in FIG. 7 under control of the control circuitry 23.

According to the first embodiment, upon receipt of a stop instruction to stop an ultrasound scan, the control circuitry 23 resets the ultrasound transmission circuitry 11 and the ultrasound reception circuitry 12. After resetting the ultrasound transmission circuitry 11 and the ultrasound reception circuitry 12, the control circuitry 23 stops the supply of a clock to the ultrasound transmission circuitry 11 and to the ultrasound reception circuitry 12.

The power consumption involved in the supply of a clock can be thereby reduced. In addition, when an ultrasound scan is restarted, a stable clock can be supplied to the ultrasound transmission circuitry 11 and to the ultrasound reception circuitry 12 each including a PLL, with the initial state, in which the PLL included in each circuitry is reset, fixed. Therefore, a malfunction of circuitry at, for example the PLL, due to an unstable clock provided during, for example, a period in which the clock has started to be provided, can be prevented.

Consequently, the power consumption during a period in which an ultrasound scan is stopped can be reduced without causing a malfunction of the ultrasound diagnostic apparatus when the ultrasound scan is restarted.

According to the first embodiment, upon receipt of a start instruction to stop an ultrasound scan, the control circuitry 23 restarts the supply of a clock to the ultrasound transmission circuitry 11 and to the ultrasound reception circuitry 12. After restarting the supply of a clock to the ultrasound transmission circuitry 11 and to the ultrasound reception circuitry 12, the control circuitry 23 cancels the reset of each of the ultrasound transmission circuitry 11 and the ultrasound reception circuitry 12. When setting a control parameter, the control circuitry 23 stores the control parameter in the parameter memory 19. Upon receipt of a restart instruction to restart an ultrasound scan, the control circuitry 23 DMA-transfers the parameters stored in the parameter memory 19 to the ultrasound transmission circuitry 11 and to the ultrasound reception circuitry 12.

The ultrasound transmission circuitry 11 and the ultrasound reception circuitry 12 each including a PLL thereby restarts a clock while in the reset state; accordingly, an ultrasound scan can be restarted without a circuitry malfunction. Furthermore, a control parameter can be directly set by means of the parameter memory 19 without the need for the host computer 24 to set a control parameter again. Namely, the time from when the freeze function is turned on to when an ultrasound scan is started can be reduced.

Second Embodiment

Described in the first embodiment is the case where reduction in power consumption of the time when an ultrasound scan is stopped is realized by controlling the supply of a clock to the ultrasound transmission circuitry 11 and to the ultrasound reception circuitry 12. Described in the second embodiment is the case where a reduction in power consumption at the time when an ultrasound scan is stopped is realized by controlling supply of power to the ultrasound transmission circuitry 11 and to the ultrasound reception circuitry 12.

Figure 8:
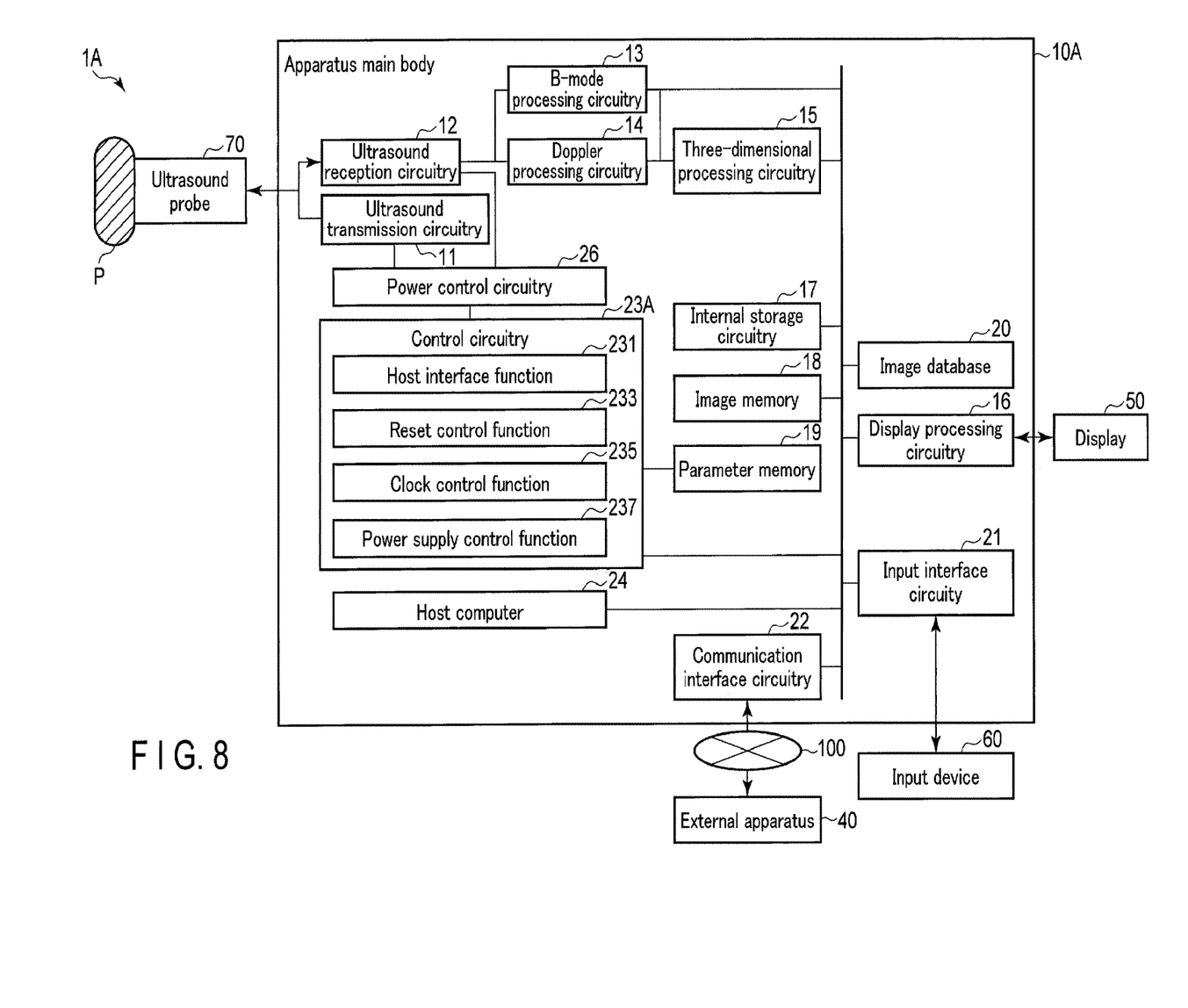
FIG. 8 is a diagram showing a configuration of an ultrasound diagnostic apparatus according to a second embodiment.

FIG. 8 is a diagram showing a configuration of an ultrasound diagnostic apparatus according to a second embodiment.

As shown in FIG. 8, the ultrasound diagnostic apparatus 1A comprises an apparatus main body 10A, an ultrasound probe 70, a display 50, and an input device 60. The apparatus main body 10 is connected to an external apparatus 40 via a network 100. The apparatus main body 10A is connected to the display 50 and the input device 60.

The apparatus main body 10A shown in FIG. 8 is an apparatus that generates an ultrasound image based on a reflected wave signal received by the ultrasound probe 70. As shown in FIG. 6, the apparatus main body 10A includes ultrasound transmission circuitry 11, ultrasound reception circuitry 12, B-mode processing circuitry 13, Doppler processing circuitry 14, three-dimensional processing circuitry 15, display processing circuitry 16, internal storage circuitry 17, an image memory 18 (cine-memory), a parameter memory 19, an image database 20, input interface circuitry 21, communication interface circuitry 22, control circuitry 23A, a host computer 24, and power supply circuitry 26.

The power supply circuitry 26 supplies power to each circuitry included in the ultrasound diagnostic apparatus 1A. The control circuitry 26 supplies power to, for example, the ultrasound transmission circuitry 11 and the ultrasound reception circuitry 12. Specifically, the power supply circuitry 26 applies a predetermined voltage to the ultrasound transmission circuitry 11 and to the ultrasound reception circuitry 12.

The control circuitry 23A is, for example, a processor that controls operations concerning an ultrasound scan. The control circuitry 23A performs an operation program stored in the internal storage circuitry 17, thereby realizing a function corresponding to the operation program. Specifically, the control circuitry 23 has a host interface function 231, a reset control function 233, and a clock control function 235, and a power supply control function 237.

The power supply control function 237 is a function of controlling the supply of power to each circuitry included in the ultrasound diagnostic apparatus 1A. When the power supply control function 237 is performed, the control circuitry 23A controls the power supply circuitry 26, and stops the supply of power to the ultrasound transmission circuitry 11 and the ultrasound reception circuitry 12 based on, for example, a stop instruction to stop an ultrasound scan. Specifically, the control circuitry 23A stops application of a voltage to the ultrasound transmission circuitry 11 and to the ultrasound reception circuitry 12. Each circuitry is thereby powered off. The control circuitry 23A may turn off the enable signal or the like of a predetermined device that generates power of each circuitry. Based on, for example, a start instruction to start an ultrasound scan, the control circuitry 23A controls the power supply control function 236, and starts the supply of power, for example, to the ultrasound transmission circuitry 11 and to the ultrasound reception circuitry 12. Specifically, the control circuitry 23A applies a predetermined voltage to the ultrasound transmission circuitry 11 and to the ultrasound reception circuitry 12.

Figure 9:
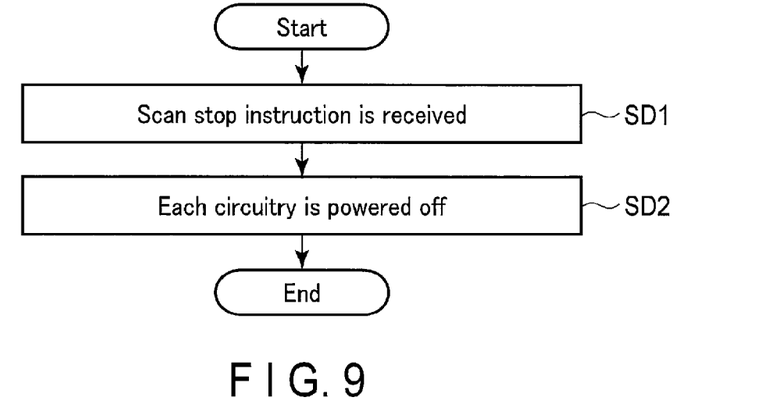
FIG. 9 is a flowchart showing an operation of the control circuitry performed when the ultrasound diagnostic apparatus according to the second embodiment receives a stop instruction to stop an ultrasound scan.
Figure 10:
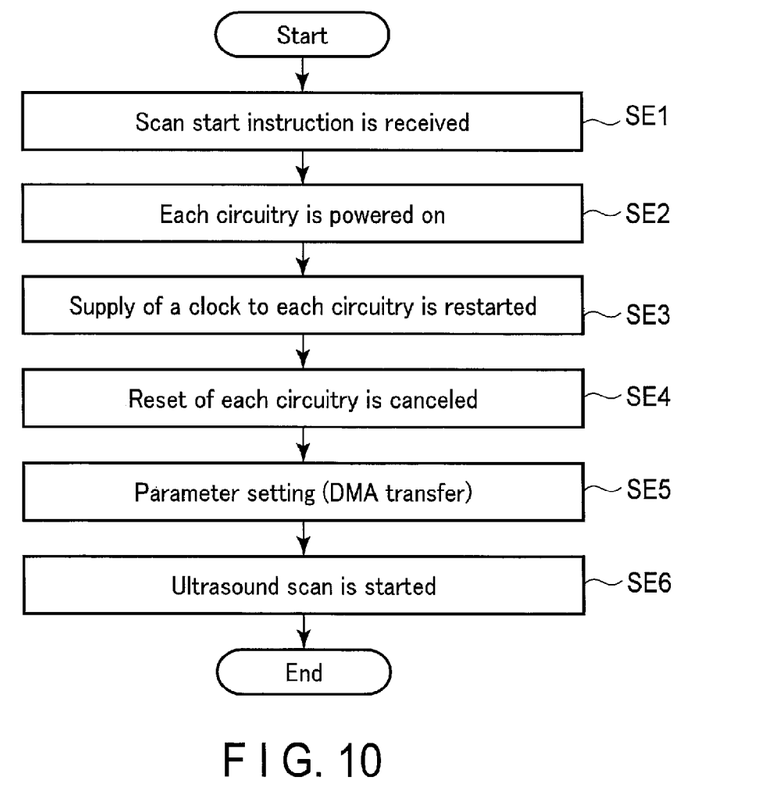
FIG. 10 is a flowchart showing an operation of the control circuitry performed when the ultrasound diagnostic apparatus according to the second embodiment receives a start instruction to start an ultrasound scan.
Figure 11:
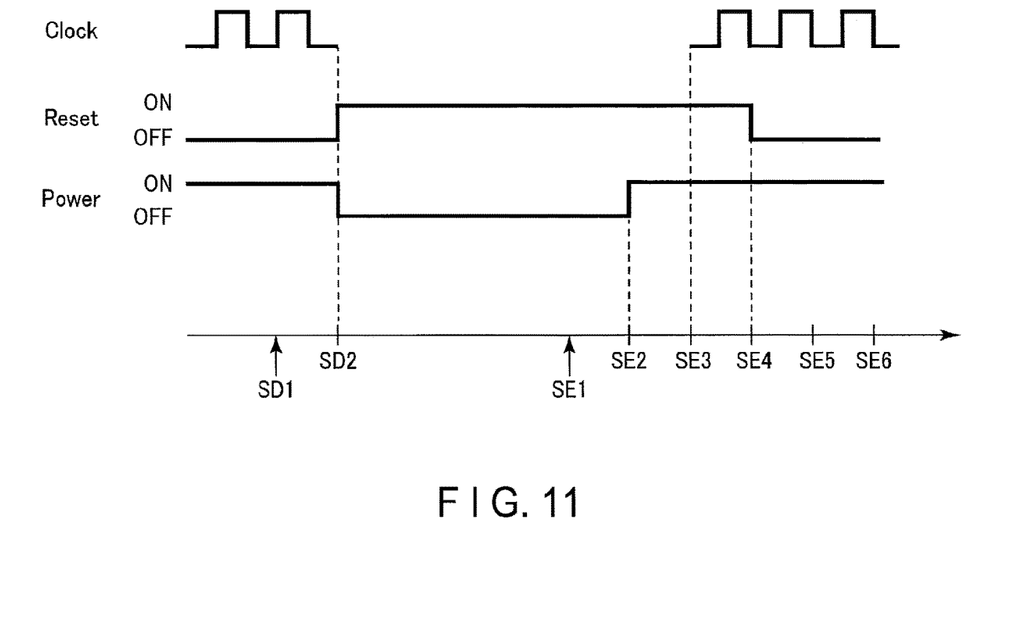
FIG. 11 is a time-sequence diagram for explaining operations of the ultrasound transmission circuitry and the ultrasound reception circuitry corresponding to the operation of the control circuitry in each step of the flowcharts shown in FIGS. 9 and 10.

Next, an operation of the ultrasound diagnostic apparatus 1A performed when an instruction to stop or start an ultrasound scan is received will be described with reference to FIGS. 9, 10, and 11. FIG. 9 is a flowchart showing an operation of the control circuitry 23A performed when the ultrasound diagnostic apparatus 1A according to the second embodiment receives a stop instruction to stop an ultrasound scan. FIG. 10 is a flowchart showing an operation of the control circuitry 23A performed when the ultrasound diagnostic apparatus 1A according to the second embodiment receives a start instruction to start an ultrasound scan. FIG. 11 is a time-sequence diagram for explaining operations of the ultrasound transmission circuitry 11 and the ultrasound reception circuitry 12 corresponding to the operation of the control circuitry 23A in each step of the flowcharts shown in FIGS. 9 and 10.

First, an operation of the ultrasound diagnostic apparatus 1A performed when a stop instruction to stop an ultrasound scan is received will be described with reference to FIGS. 9 and 11. In the following description, let us assume that an operation to turn on the freeze function is performed by pressing the freeze button provided in the ultrasound probe 70, for example. At this time, a stop instruction to stop an ultrasound scan is input to the host computer 24. Then, the host computer 24 notifies the control circuitry 23A of the input stop instruction. In the second embodiment, the control circuitry 23A directly powers off the ultrasound transmission circuitry 11 and the ultrasound reception circuitry 12, and need not reset the ultrasound transmission circuitry 11 or the ultrasound reception circuitry 12.

In FIG. 9, the control circuitry 23A performs the host interface function 231, and receives from the host computer 24 an instruction to stop an ultrasound scan (step SD1). At this time, the ultrasound transmission circuitry 11 and the ultrasound reception circuitry 12 are provided with a clock as shown in FIG. 11. Furthermore, the ultrasound transmission circuitry 11 and the ultrasound reception circuitry 12 are in the non-reset state as shown in FIG. 11.

In FIG. 9, the control circuitry 23A performs the power supply control function 237, and powers off the ultrasound transmission circuitry 11 and the ultrasound reception circuitry 12 (step SD2). Specifically, the control circuitry 23A controls the power supply circuitry 26 to stop the supply of power to the ultrasound transmission circuitry 11 and to the ultrasound reception circuitry 12. At this time, for example, the ultrasound transmission circuitry 11 and the ultrasound reception circuitry 12 are powered off as shown in FIG. 11.

Next, an operation of the ultrasound diagnostic apparatus 1, performed when a start instruction to start an ultrasound scan is received again after an ultrasound scan is stopped, will be described with reference to FIGS. 10 and 11. In the following description, let us assume that an operation to turn off the freeze function is performed by pressing the freeze button provided in the ultrasound probe 70, for example. At this time, a start instruction to start an ultrasound scan is input to the host computer 24. Then, the host computer 24 notifies the control circuitry 23A of the input start instruction.

In FIG. 10, the control circuitry 23A performs the host interface function 231, and receives from the host computer 24 an instruction to start an ultrasound scan (step SE1). At this time, the ultrasound transmission circuitry 11 and the ultrasound reception circuitry 12, etc. are off as shown in FIG. 11.

In FIG. 10, the control circuitry 23A performs the power supply control function 237, and powers on the ultrasound transmission circuitry 11 and the ultrasound reception circuitry 12 (step SE2). Specifically, the control circuitry 23A controls the power supply circuitry 26 to restart the supply of power to the ultrasound transmission circuitry 11 and to the ultrasound reception circuitry 12. At this time, for example, the ultrasound transmission circuitry 11 and the ultrasound reception circuitry 12 are powered on as shown in FIG. 11.

In FIG. 10, the control circuitry 23A performs the clock control function 235, and restarts the supply of a clock to the ultrasound transmission circuitry 11 and to the ultrasound reception circuitry 12 (step SE3). At this time, the supply of a clock to the ultrasound transmission circuitry 11 and to the ultrasound reception circuitry 12 is started as shown in FIG. 11.

In FIG. 10, after restarting the supply of a clock to the ultrasound transmission circuitry 11 and to the ultrasound reception circuitry 12, the control circuitry 23A performs the reset control function 233, and cancels the reset of the ultrasound transmission circuitry 11 and the reset of the ultrasound reception circuitry 12 (step SE4). At this time, the reset of the ultrasound transmission circuitry 11 and the reset of the ultrasound reception circuitry 12 are canceled (the ultrasound transmission circuitry 11 and the ultrasound reception circuitry 12 are brought into a reset-OFF state) as shown in FIG. 11.

In FIG. 10, the control circuitry 23A performs the host interface function 231, refers to address association information stored in the predetermined internal memory included in the control circuitry 23A, and reads a control parameter from the parameter memory 19. The control circuitry 23A DMA-transfers the read control parameter to the ultrasound transmission circuitry 11 and to the ultrasound reception circuitry 12. Then, the control circuitry 23A sets the control parameter for each of the ultrasound transmission circuitry 11 and the ultrasound reception circuitry 12 (step SE5). Accordingly, parameter setting can be performed without intervention of the host computer 24.

In FIG. 10, the control circuitry 23A controls the ultrasound transmission circuitry 11 and the ultrasound reception circuitry 12 to start an ultrasound scan (step SE6). At this time, the ultrasound transmission circuitry 11 and the ultrasound reception circuitry 12 start an ultrasound scan as shown in FIG. 11 under control of the control circuitry 23A.

According to the second embodiment, upon receipt of a stop instruction to stop an ultrasound scan, the control circuitry 23A controls the power supply circuitry 26, and stops the supply of power to the ultrasound transmission circuitry 11 and to the ultrasound reception circuitry 12.

In general, setting of a parameter necessary for restarting an ultrasound scan after power is turned on is performed for each circuitry via the host computer 24. The intervention of the host computer 24 increases the time required for setting. According to the second embodiment, the ultrasound diagnostic apparatus 1A reads a control parameter from the parameter memory 19 and DMA-transfers the read control parameter to each circuitry to set a control parameter for each circuitry. Without intervention of the host computer 24, the time from when the freeze function is turned on to when an ultrasound scan is started can be reduced.

Other Embodiments

In the above-described first and second embodiments, the power consumption of the ultrasound transmission circuitry 11 and the ultrasound reception circuitry 12 of the circuitries of the ultrasound diagnostic apparatus is reduced; however, the circuitry of which power consumption is reduced is not limited to those circuitries. The circuitry of which power consumption is reduced may be any circuitry used for an ultrasound scan, for example.

Figure 12:
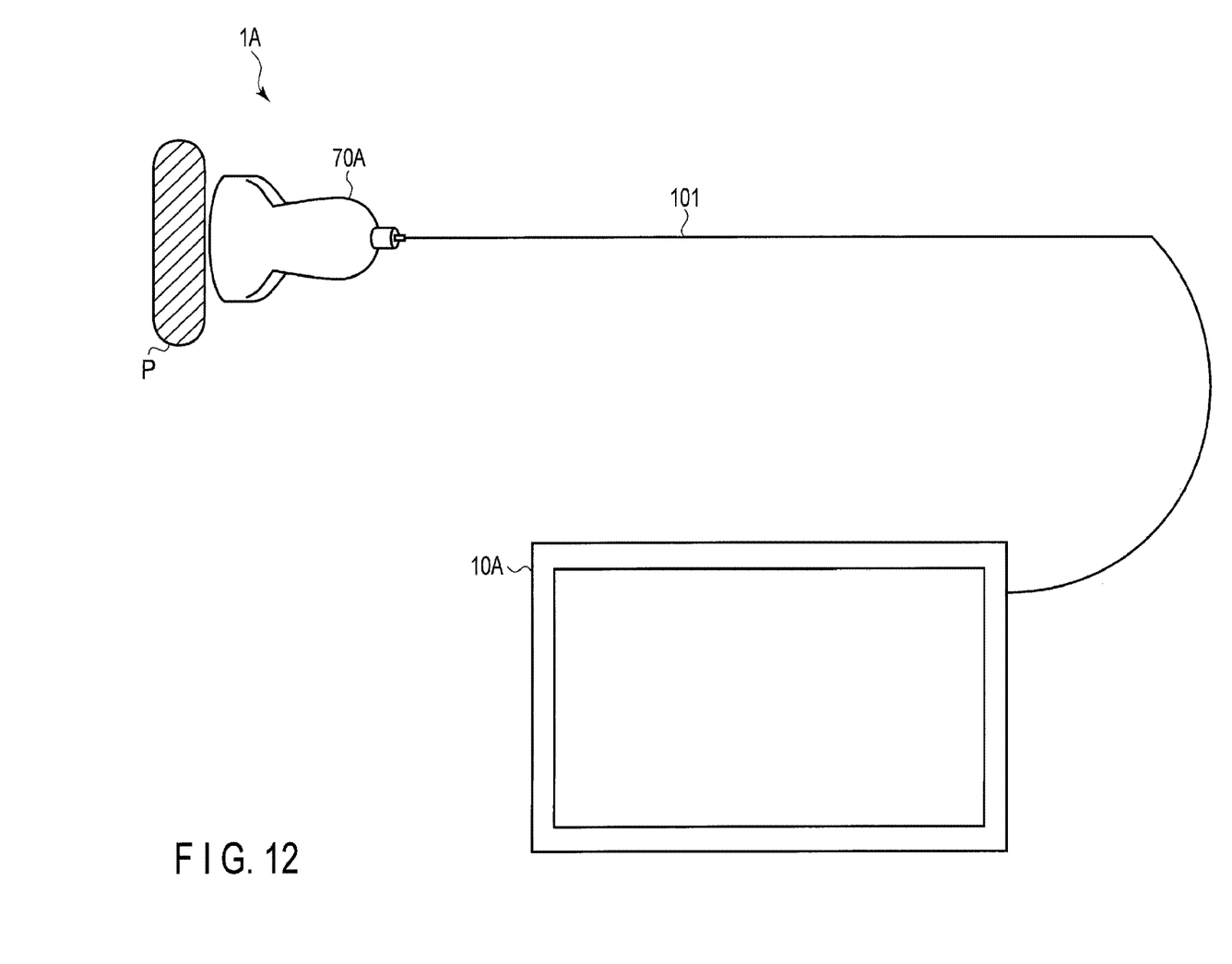
FIG. 12 is a diagram showing an exterior of a potable ultrasound diagnostic apparatus according to another embodiment.

The type of the ultrasound diagnostic apparatus is not limited to the stationary type, and may be the portable type. FIG. 12 is a diagram showing an example of the exterior of a portable type ultrasound diagnostic apparatus 1A according to another embodiment. In FIG. 12, the ultrasound diagnostic apparatus 1A includes an ultrasound probe 70A and an apparatus main body 10A. The ultrasound probe 70A is connected to the apparatus main body 2 by, for example, a digital bus 101 using a wired universal cable. The digital bus 101 is, for example, a universal serial bus (USE). The universal cable used for the digital bus 101 can be inserted in and pulled out from the apparatus main body 10A. The ultrasound probe 70A may be wirelessly connected to the apparatus main body 10A.

The ultrasound probe 70A includes, for example, the ultrasound transmission circuitry 11 and the ultrasound reception circuitry 12 included in the apparatus main body 10 shown in FIG. 1, in addition to the structures included in the ultrasonic probe 70 shown in FIG. 1. Power of the ultrasound probe 70A is supplied from the apparatus main body 10A via the universal cable, for example. When the ultrasound probe 70A is wirelessly connected to the apparatus main body 10A, a battery or the like that supplies power to the ultrasound probe 70A may be provided. At this time, the ultrasound probe 70A is driven by the battery.

The apparatus main body 10A is, for example, a tablet-type information terminal. The apparatus main body 10A may be, for example, a portable personal computer (PC). The apparatus main body 10A includes, for example, the structures of the apparatus main body 10 shown in FIG. 1 other than the ultrasound transmission circuitry 11 and the ultrasound reception circuitry 12. The apparatus main body 10A also includes, for example, a battery, and is driven by the battery.

As described above, unlike stationary ultrasound diagnostic apparatuses, the portable type ultrasound diagnostic apparatus 1A according to another embodiment is, for example, driven by a built-in battery, which makes a reduction in power consumption more significant.

In the ultrasound diagnostic apparatus 1A, the ultrasound probe 70A may include, for example, the B-mode processing circuitry 13 and the Doppler processing circuitry 14 shown in FIG. 1. This eliminates the need to mount, for example, the B-mode processing circuitry 13 and the Doppler processing circuitry 14 on the apparatus main body 10A, and can improve versatility of the apparatus main body 10A.

In the ultrasound diagnostic apparatus 1A, the ultrasound probe 70A may also include the three-dimensional processing circuitry 15 shown in FIG. 1, in addition to the B-mode processing circuitry 13 and Doppler processing circuitry 14 shown in FIG. 1. This eliminates the need to mount the B-mode processing circuitry 13, the Doppler processing circuitry 14, and the three-dimensional processing circuitry 15 on the apparatus main body 10A, and can further improve versatility of the apparatus main body 10A.

The term "processor" used in the above description means, for example, a central processing unit (CPU), a graphics processing unit (GPU), or circuitry such as an application specific integrated circuit (ASIC), a programmable logic device (e.g., a simple programmable logic device (SPLD), a complex programmable logic device (CPLD), or a field programmable gate array (FPGA). The processor realizes a function by reading and executing a program stored in the memory circuitry. Each processor of the above-described embodiments is not necessarily configured as a single circuit, and a plurality of independent circuits may be configured in combination as one processor to realize the function. In addition, a plurality of structural elements in FIGS. 1 and 8 may be integrated in one processor to realize the function.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasound diagnostic apparatus comprising:
a memory that stores a parameter necessary for starting an ultrasound scan;
at least one circuitry used for the ultrasound scan; and
control circuitry configured to:
reset the at least one circuitry upon receipt of a stop instruction to stop the ultrasound scan;
stop supply of a clock to the at least one circuitry;
restart the supply of the clock to the at least one circuitry upon receipt of a start instruction to start the ultrasound scan when the at least one circuitry is in a reset state;
cancel the reset of the at least one circuitry after restarting the supply of the clock;
read the parameter stored in the memory; and
set the read parameter for the at least one circuitry without accessing a host computer,
wherein resetting the at least one circuitry comprises fixing at least one switching element included in the at least one circuitry in a predetermined initial state, and
canceling the reset of the at least one circuitry comprises ending the fixed predetermined initial state so that the at least one switching element is changeable.

2. The ultrasound diagnostic apparatus according to claim 1, further comprising
power supply circuitry configured to control the supply of power to the at least one circuitry,
wherein, upon receipt of the stop instruction to stop the ultrasound scan, the power supply circuitry is configured to stop the supply of power to the at least one circuitry.

3. An ultrasound diagnostic apparatus according to claim 1,
wherein the start instruction is input by an operator.

4. A method of reducing power consumption, the method comprising:
storing a parameter necessary for starting an ultrasound scan;
resetting at least one circuitry used for the ultrasound scan upon receipt of a stop instruction to stop an ultrasound scan;
stopping the supply of a clock to the at least one circuitry;
restarting the supply of the clock to the at least one circuitry upon receipt of a start instruction to start the ultrasound scan when the at least one circuitry is in a reset state;
canceling the reset of the at least one circuitry after restarting the supply of the clock;
reading the parameter stored in the memory; and
setting the read parameter for the at least one circuitry without accessing a host computer,
wherein resetting the at least one circuitry comprises fixing at least one switching element included in the at least one circuitry in a predetermined initial state, and
canceling the reset of the at least one circuitry comprises ending the fixed predetermined initial state so that the at least one switching element is changeable.

* * * * *